US00PP23182P2

(12) United States Plant Patent
Bergman

(10) Patent No.: US PP23,182 P2
(45) Date of Patent: Nov. 13, 2012

(54) ***CHRYSANTHEMUM* PLANT NAMED 'CIDZ0016'**

(50) Latin Name: *Chrysanthemum×morifolium*
Varietal Denomination: CIDZ0016

(75) Inventor: Wendy R. Bergman, Gilroy, CA (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 13/136,484

(22) Filed: Aug. 2, 2011

(51) Int. Cl.
*A01H 5/00* (2006.01)

(52) U.S. Cl. ..... Plt./298

(58) Field of Classification Search ..... Plt./298
See application file for complete search history.

*Primary Examiner* — Annette Para
(74) *Attorney, Agent, or Firm* — Joshua L. Price

(57) ABSTRACT

A new *Chrysanthemum* plant named 'CIDZ0016' particularly distinguished by the bright red ray floret color, medium green foliage, six weeks flowering response, smaller sized foliage, very compact growth habit and is very freely branching.

1 Drawing Sheet

Latin name of the genus and species of the plant claimed: *Chrysanthemum×morifolium.*

Varietal denomination: 'CIDZ0016'.

BACKGROUND OF THE NEW PLANT

The present invention comprises a new *Chrysanthemum*, botanically known as *Chrysanthemum×morifolium*, and hereinafter referred to by the variety name 'CIDZ0016'.

'CIDZ0016' is a product of a planned breeding program. The new cultivar has bright red ray floret color, medium green foliage, six weeks flowering response, smaller sized foliage, very compact growth habit and is very freely branching.

'CIDZ0016' originated from a hybridization made in April 2007 in a controlled breeding environment in Salinas, Calif., USA. The female parent was the proprietary plant designated 'YB-A8602', unpatented, with yellow inflorescences with and a bronze halo, and a less compact habit.

The male parent of 'CIDZ0016' was an unpatented plant identified as 'YB-A7240' with larger purple flowers. The resultant seed was sown in October 2007 in Fort Myers, Fla., USA.

'CIDZ0016' was selected as one flowering plant within the progeny of the stated cross in March 2008 in a controlled environment in Fort Myers, Fla., USA.

The first act of asexual reproduction of 'CIDZ0016' was accomplished when vegetative cuttings were propagated from the initial selection in June 2008 in a controlled environment in Fort Myers, Fla., USA.

BRIEF SUMMARY OF INVENTION

Horticultural examination of plants grown from cuttings of the plant initiated in June 2008, and continuing thereafter, has demonstrated that the combination of characteristics as herein disclosed for 'CIDZ0016' are firmly fixed and are retained through successive generations of asexual reproduction.

'CIDZ0016' has not been observed under all possible environmental conditions. The phenotype may vary significantly with variations in environment such as temperature, light intensity and day length.

A Plant Breeder's Right for this cultivar was applied for in Canada on Aug. 17, 2010 (10-7075). 'CIDZ0016' has not been made publicly available more than -one year prior to the filing of this application.

The following traits have been repeatedly observed and are determined to be basic characteristics of the new variety. The combination of these characteristics distinguishes this *Chrysanthemum* as a new and distinct variety.

BRIEF DESCRIPTION OF THE PHOTOGRAPHS

The accompanying photographic drawing shows typical flower and foliage characteristics of 'CIDZ0016' with colors being as true as possible with an illustration of this type. The photographic drawing shows a flowering potted plant of the new variety and a close-up of the flowers.

DETAILED BOTANICAL DESCRIPTION

The plant descriptions, measurements and aforementioned photographs were taken in Gilroy, Calif. in early May 2011 under natural light. These plants were propagated and grown in Nipomo, Calif. and shipped to Gilroy, Calif. for the data collection and photographs. These plants were approximately 11 weeks of age; grown with three plants together in a five inch bulb pan under greenhouse trial conditions.

Color references are made to The Royal Horticultural Society Colour Chart (R.H.S.) 2001.

TABLE 1

DIFFERENCES BETWEEN THE NEW VARIETY 'CIDZ0016' AND A SIMILAR VARIETY

| | 'CIDZ0016' | 'Currant Yomistique' (U.S. Plant Pat. No. 20,197) |
|---|---|---|
| Inflorescence size: | Smaller | Larger |
| Ray floret color: | More red | Less red |
| Ray floret length: | Longer | Shorter |

Plant:
*Form, growth and habit.*—Herbaceous fleurette pot type, stems upright and outwardly spreading, freely branching.
*Plant height.*—8.-9.0 cm.
*Plant height (inflorescence included).*—12.-15.0 cm.
*Plant width.*—10.-12.0 cm.
Roots:
*Number of days to initiate roots.*—About 4 days at about 22 degrees C.
*Number of days to produce a rooted cutting.*—About 10 days at 22 degrees C.
*Type.*—Fine, fibrous, free branching.
*Color.*—RHS N155B but whiter.
Foliage:
*Arrangement.*—Alternate, simple.
*Immature, leaf color, upper surface.*—Between RHS 137B and RHS 137C.
*Lower surface.*—Between RHS 137C and RHS 137D.
*Mature, leaf color, upper surface.*—Between RHS 137B and RHS 137C.
*Lower surface.*—Between RHS 137C and RHS 137D.
*Length.*—3.9-4.1 cm.
*Width.*—2.6-2.7 cm.
*Shape.*—Ovate.
*Base shape.*—Attenuate.
*Apex shape.*—Mucronulate.
*Margin.*—Palmately lobed to irregularly serrate.
*Texture, upper surface.*—Bifid T-shaped hairs.
*Lower surface.*—Bifid T-shaped hairs.
*Color of veins, upper surface.*—RHS 138B.
*Color of veins, lower surface.*—RHS 138B.
*Petiole color.*—RHS 138B.
*Length.*—1.1-1.2 cm.
*Diameter.*—0.2 cm.
*Texture.*—Bifid T-shaped hairs.
Stem:
*Quantity of main branches per plant.*—4-5.
*Color of stem.*—RHS 138A but appears lighter due to hairs.
*Length of stem.*—7-10 cm.
*Diameter.*—0.3 cm.
*Length of internodes.*—0.4-0.7 cm.
*Texture.*—Heavily bifid T-shaped hairs.
*Color of peduncle.*—RHS 138A but appears lighter due to hairs.
*Length of peduncle.*—2.3-3.0 cm.
*Peduncle diameter.*—0.1 cm.
*Texture.*—Heavily bifid T-shaped hairs.
Inflorescence:
*Type.*—Compositae type, solitary daisy-type inflorescences, borne terminally above foliage, ray florets arranged acropetally on a capitulum.
*Quantity of short days to flowering (response time).*—About 6 weeks.
*Quantity of inflorescences per plant.*—25-35.
*Lastingness of individual blooms on the plant.*—About 4 weeks.
*Fragrance.*—Slightly spicy.
Bud (just when opening/showing color):
*Color.*—RHS 181A but a little deeper.
*Length.*—0.7-0.9 cm.
*Width.*—0.5 cm.
*Shape.*—Oblate.
Immature inflorescence:
*Diameter.*—2.6-2.9 cm.
*Color of ray florets, upper surface.*—RHS 53A but darker.
*Lower surface.*—RHS 181A to RHS 181B.
Mature inflorescence:
*Diameter.*—3.5-3.8 cm.
*Depth.*—1.3 cm.
*Total diameter of 'disc'.*—1.0-1.3 cm.
*Receptacle height.*—0.3 cm.
*Receptacle diameter.*—0.4 cm.
Ray florets:
*Average quantity of florets.*—19-20 in 1-2 whorls.
*Color of florets, upper surface.*—Closest to RHS N34A but more silvery-grey overlay, fading to mottled RHS 181A to RHS 181B.
*Lower surface.*—A silvery RHS 181A and lighter at the margins.
*Length.*—1.7-1.9 cm.
*Width.*—0.6-0.65 cm.
*Shape.*—Elliptical.
*Apex shape.*—Irregularly emarginate.
*Margin.*—Entire.
*Texture, upper surface.*—Papillose.
*Lower surface.*—Papillose.
Disc florets:
*Average quantity of florets.*—Approximately 150.
*Color of florets.*—RHS 1C with RHS 7B apex.
*Length.*—0.5-0.6 cm.
*Width.*—0.1 cm.
*Shape.*—Tubular, elongated.
*Apex shape.*—Acute, 5 pointed.
Phyllaries:
*Quantity.*—Approximately 15.
*Color, upper surface.*—RHS 138A but appears lighter due to hairs.
*Lower surface.*—RHS 138A.
*Length.*—0.3-0.45 cm.
*Width.*—0.15-0.2 cm.
*Shape.*—Lanceolate.
*Apex shape.*—Obtuse.
*Base.*—Fused.
*Margins.*—Entire.
*Texture, upper surface.*—Glabrous.
*Lower surface.*—Bifid T-shaped hairs.
Reproduction organs:
*Pistil.*—1.
*Found on both florets.*—Yes.
*Length.*—0.5 cm.
*Style color.*—RHS 1C.
*Style length.*—0.45 cm.
*Stigma color.*—RHS 7A.
*Stigma shape.*—Bi-parted.
*Ovary color.*—Not observed.
*Stamens.*—1.
*Found on only disc florets.*—Yes.
*Color of filaments.*—Not observed.
*Length filaments.*—Not observed.
*Anther color.*—Not observed.
*Anther length.*—Not observed.
*Anther shape.*—Not observed.

*Color of pollen*.—Not observed.

*Pollen amount*.—Not observed.

*Fertility/seed set*.—Has not been observed on this hybrid.

Disease/pest resistance: Disease/pest resistance has not been observed on this hybrid.

What is claimed is:

1. A new and distinct variety of *Chrysanthemum* plant named 'CIDZ0016' substantially as illustrated and described herein.

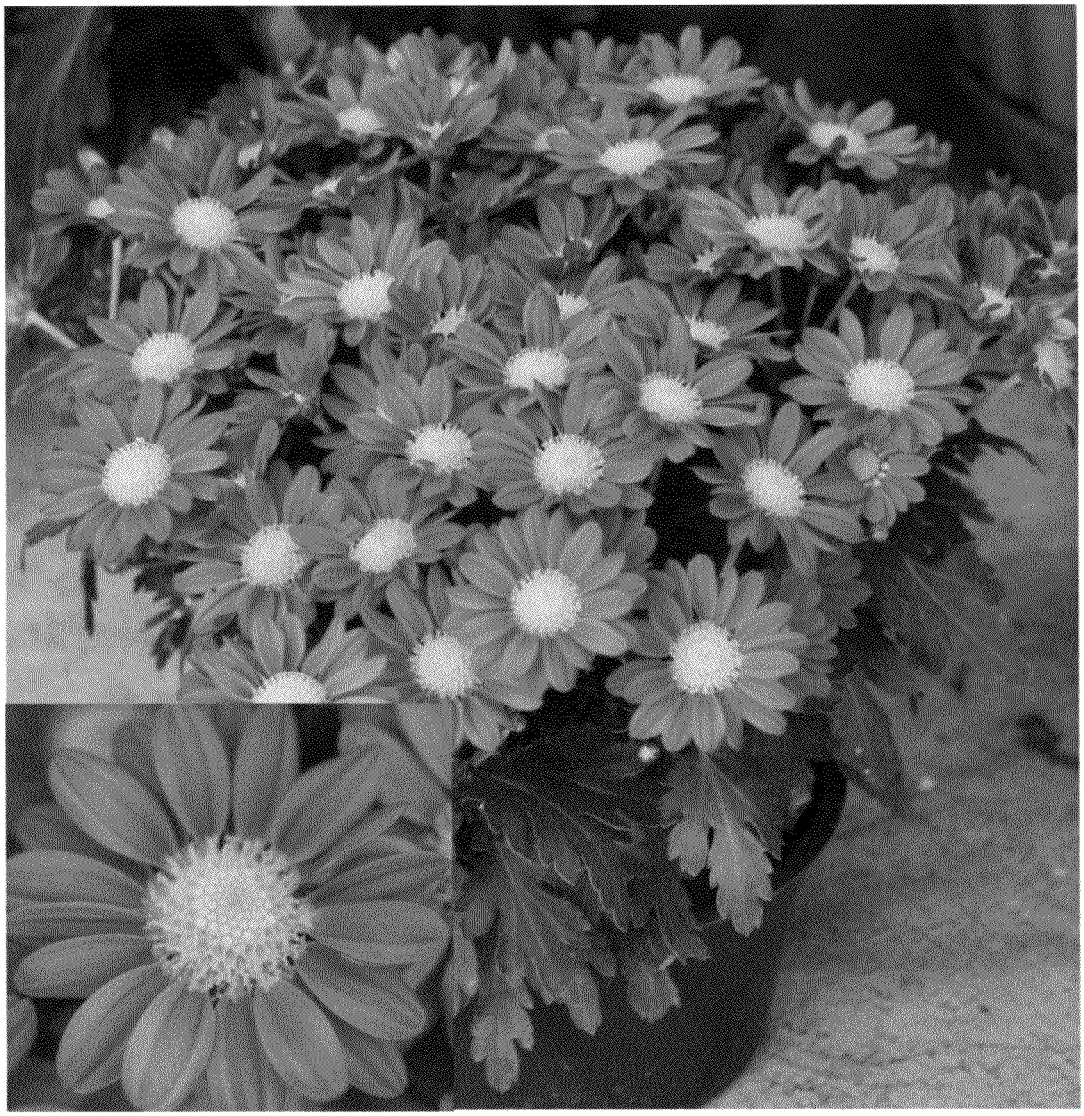

* * * * *